United States Patent
Hughes et al.

(10) Patent No.: US 7,528,958 B2
(45) Date of Patent: May 5, 2009

(54) OPTICAL SCANNER FOR MEASURING SHEET PROPERTIES

(75) Inventors: Michael K Y Hughes, Vancouver (CA); Sebastien Tixier, North Vancouver (CA)

(73) Assignee: Honeywell International Inc., Morristown, NJ (US)

( * ) Notice: Subject to any disclaimer, the term of this patent is extended or adjusted under 35 U.S.C. 154(b) by 255 days.

(21) Appl. No.: 11/323,715

(22) Filed: Dec. 30, 2005

(65) Prior Publication Data

US 2007/0153286 A1 Jul. 5, 2007

(51) Int. Cl. *G01B 9/02* (2006.01)
(52) U.S. Cl. ...................................... 356/455
(58) Field of Classification Search ................. 356/451, 356/455, 497, 503
See application file for complete search history.

(56) References Cited

U.S. PATENT DOCUMENTS

| | | | | |
|---|---|---|---|---|
| 3,813,174 A | * | 5/1974 | Nowak et al. | 356/241.1 |
| 4,632,560 A | | 12/1986 | Stringfield | |
| 4,813,782 A | * | 3/1989 | Yagi et al. | 356/507 |
| 5,094,535 A | | 3/1992 | Dahlquist et al. | |
| 5,541,731 A | * | 7/1996 | Freedenberg et al. | 356/496 |
| 5,648,849 A | * | 7/1997 | Canteloup et al. | 356/503 |
| 6,057,920 A | * | 5/2000 | Fercher et al. | 356/497 |
| 6,356,846 B1 | * | 3/2002 | Habeger et al. | 702/40 |
| 2003/0090655 A1 | * | 5/2003 | Norton et al. | 356/326 |

FOREIGN PATENT DOCUMENTS

DE 2152510 A1 4/1972

OTHER PUBLICATIONS

E. Lafond et al., "A Noncontact, On-machine, Laser Ultrasonic Sensor for Measuring Paper and paperboard Bending Stiffness and Shear Rigidities", Proceedings of TAPPI Practical Papermaking Conference, May 23, 2005.
Slide Presentation made at the Proceedings of TAPPI Practical Papermaking Conference of May 23, 2005 by E. Lafond et al., "A Noncontact, On-machine, Laser Ultrasonic Sensor for Measuring Paper and paperboard Bending Stiffness and Shear Rigidities".

* cited by examiner

*Primary Examiner*—Samuel A Turner
(74) *Attorney, Agent, or Firm*—Scully, Scott, Murphy & Presser (57) ABSTRACT

An optical scanner for use in conjunction with an infrared spectrometer is disclosed. The optical scanner translates a beam of radiation to a stationary spot on a traveling sheet of material so that ample integration time within the spectrometer is achieved. The beam path impinges on the traveling web and the radiation is reflected off the traveling web back through the optical scanner and recombined at an interferometer. The beam of radiation is kept stationary with respect to both the traveling sheet and the carriage which houses the spectrometer.

22 Claims, 6 Drawing Sheets

PRIOR ART

OPTICAL SCANNER FOR MEASURING SHEET PROPERTIES

FIELD OF THE INVENTION

The invention relates to optical scanners for measuring the properties of sheet materials, and more particularly, to an optical scanner for conjunction with a spectrometer for measuring the properties of plastic and paper sheets.

DISCUSSION OF THE PRIOR ART

Figure 1:
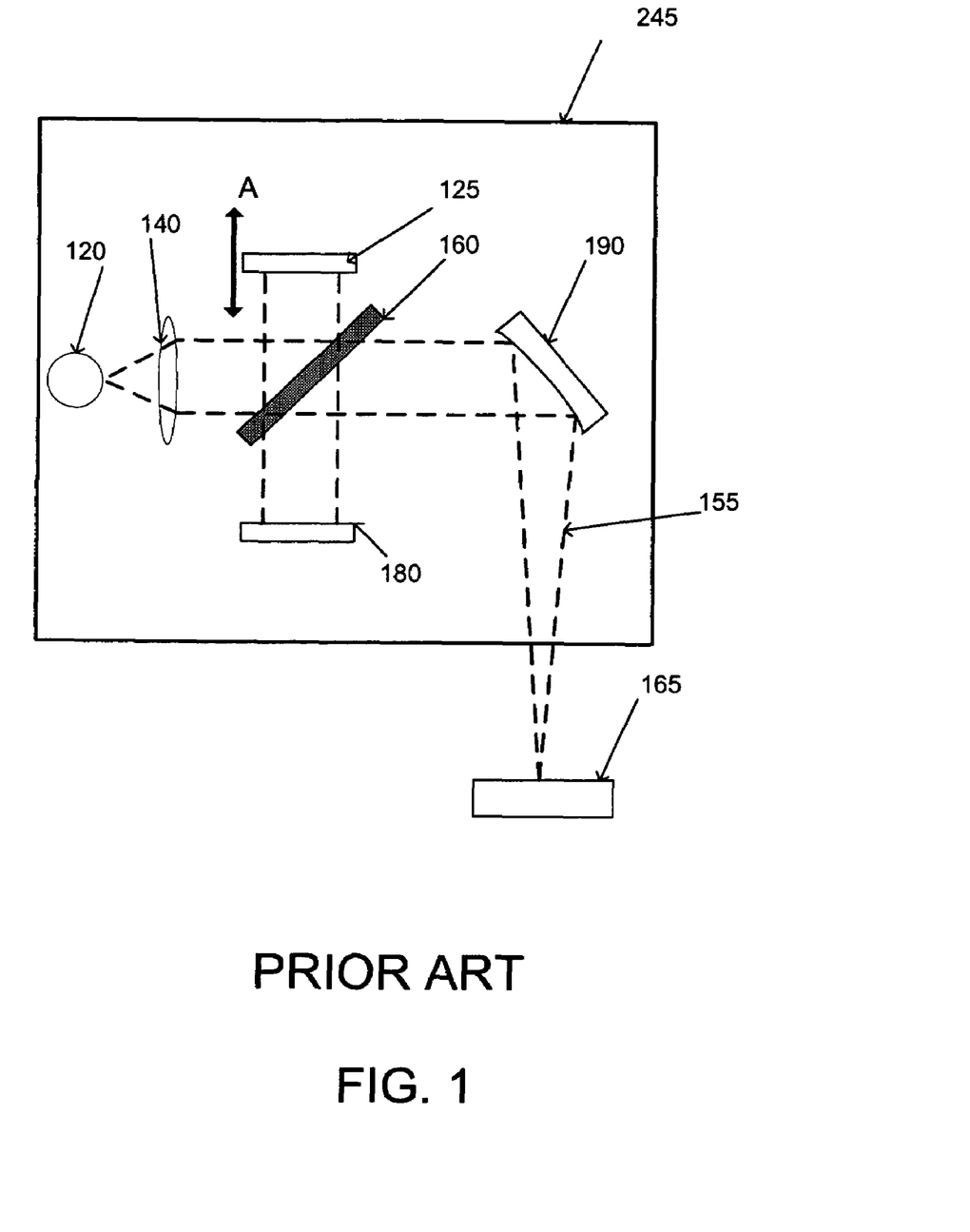
FIG. 1 is a schematic diagram of a conventional Fourier Transform Infrared spectrometer.

Spectrometers are well known in the art. Various types of spectrometers are used in analyzing and identifying characteristics of various sample materials. Referring to FIG. 1, there is shown a conventional Fourier Transform Infrared (FT-IR) spectrometer 100. The spectrometer includes an infrared source 120. Radiation from source 120 is collimated by a lens 140. The resultant beam (shown in dotted lines) passes to and is divided by a beam splitter 160. Half of the beam is passed to a fixed mirror 180, and half is directed to a moving mirror 125. Moving mirror 125 is movable in the directions of arrow A as indicated in the figure.

The split beam is reflected by mirrors 180 and 125, recombines at beam splitter 160 and constructively or destructively interferes depending on the difference in the length of the optical paths between mirrors 180 and 125 and the beam splitter.

During operation of the spectrometer, moving mirror 125 moves at a velocity in one direction. As a result, a beam emerges from the beam splitter which is a mixture of modulated frequencies. This mixture is reflected off a mirror 190 onto a path 155. Path 155 passes through a window 165 which supports a sample material to be analyzed.

Generally, spectrometers may be operated in one of two modes, transmission and reflection modes. Referring back to FIG. 1, when the FT-IR spectrometer is operated in a transmission mode, the window is made from a material that allows radiation in the infrared range to pass therethrough without substantial absorption. An infrared detector (not shown) is placed on the opposite side of the FT-IR spectrometer from the sample. After the radiation passes through the sample, the resultant radiation is focused on the infrared detector where signals are generated in response to the amplitude of the sensed radiation. These signals are sampled by the FT-IR spectrometer at predetermined intervals to produce an interferogram which is unique to the sample material.

When the FT-IR spectrometer is operated in a reflection mode, the path 155 of the infrared radiation impinges on a sample to be analyzed. Unlike the window used when the spectrometer is operated in transmission mode, the window is reflective to the infrared radiation. As a result, the radiation bounces off the window and is passed through the sample a second time before finally passing to the detector. This double pass through the sample provides better, more accurate scanning and analysis in many cases.

In the paper and plastics industries, sheet properties such as thickness and other characteristics can be measured by use of a grating spectrometer by placing the sheet material in the sample window. In either the transmission or reflection mode, an important characteristic of many grating spectrometers is the integration time period required for making a proper reading on the spectrometer. The integration time period is typically the time required for the charge coupled devices on a linear array detector to account for all of the photons to excite all of the pixels of the detector. For infrared spectrometry, the integration times are extremely short (approximately 1 ms). This typically requires that the sample be stationary with respect to the grating spectrometer during the integration time period. In a laboratory environment, this should not be a problem. However, in an on-line manufacturing environment, particularly for the paper and plastics industries, the use of grating spectrometers is limited due to the short integration times.

Furthermore, variations in the thickness of the sheet material during integration time results in a washing out of the interference pattern. In spectroscopic techniques, it is desirable to use single channel detectors and acousto-optic tunable filters in order to measure infrared regions of interest. The problem with this technique is that the entire spectrum can usually not be measured simultaneously. The movement of the sheet leads to inaccuracy in the measured properties. Measuring a stationary spot on the sheet can increase the accuracy. It may be possible to use a flash of light to overcome the integration time problem with thin film interferometry. However, suitable sources in the near infrared are unavailable and mechanical choppers for infrared sources have inherent limitations.

One approach for compensating for the traveling sheet is disclosed in "A Noncontact, On-machine, Laser Ultrasonic Sensor for Measuring Paper and Paperboard Bending Stiffness and Shear Rigidities," E. Lafond, et al., *Proceedings of TAPPI Practical Papermaking Conference* (May 23, 2005). Lafond describes the use of an ultrasonic laser coupled to a servomechanism for measuring the shear properties of paper in a papermaking machine.

Although, an acoustic approach may be suitable for measuring the shear properties of paper in a papermaking machine, other properties may only be measured in the optical domain. For instance, an ultrasonic approach may not be suitable when the sample is a thin film (on the order of 8 µm). Therefore, it would be highly desirable for an approach that uses radiation in the optical domain.

BRIEF SUMMARY OF THE INVENTION

The present invention provides an optical scanner for use in conjunction with a spectrometer for measuring sheet properties. The optical scanner allows for the same spot in a traveling web of sheet materials to be observed in a spectrometer so that interference patterns can be observed without regard to the varying thicknesses in a traveling web of sheet materials.

In one aspect, the invention is an infrared spectrometer for measuring properties of traveling sheet material, said spectrometer comprising: a source for emitting radiation towards the traveling sheet material; a beam splitter for splitting the emitted radiation; an optical scanner for directing the emitted radiation towards the traveling sheet material; and a detector for measuring the radiation after interaction with the traveling sheet material, wherein said optical scanner is configured for scanning the radiation to counteract the movement of the traveling sheet material.

In another aspect, the invention is an optical scanner for use in conjunction with an infrared spectrometer, said infrared spectrometer configured for measuring properties of traveling sheet material, said spectrometer comprising a radiation source for emitting radiation, a beam splitter for splitting the emitted radiation, and a detector for measuring the radiation after interaction with the traveling sheet material, said optical scanner comprising: oscillating beam deflecting means for keeping a beam of the radiation stationary with respect to the traveling sheet material; and driving means for driving said oscillating beam deflecting means.

BRIEF DESCRIPTION OF THE DRAWINGS

The invention is further described in the detailed description that follows, by reference to the noted drawings by way of non-limiting illustrative embodiments of the invention, in which like reference numerals represent similar parts throughout the drawings. As should be understood, however, the invention is not limited to the precise arrangements and instrumentalities shown. In the drawings.

DETAILED DESCRIPTION OF THE INVENTION

Reference will now be made in detail to the preferred embodiments of the present invention, a spectroscopic sensor for measuring sheet properties, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, components, and circuits have not been described in detail as not to unnecessarily obscure aspects of the present invention.

Some portions of the detailed descriptions which follow are presented in terms of procedures, steps, logic blocks, processing, and other symbolic representations of operations on radiation signals. These descriptions and representations are the means used by those skilled in the data processing arts to most effectively convey the substance of their work to others skilled in the art. A procedure, computer executed step, logic block, process, etc., is here, and generally, conceived to be a self-consistent sequence of steps or instructions leading to a desired result. The steps are those requiring physical manipulations of physical quantities.

To illustrate the principles of the invention, it may be helpful to generally describe the manufacturing environment in the paper and plastics industries. Typically a large carriage traverses sheet materials perpendicular to the traveling sheet motion to scan for imperfections and for quality control. Therefore, in an on-line manufacturing environment, it may be preferable to have the optical beam be stationary with respect to the direction of the traveling sheet and the direction of the carriage. Both movements must be compensated for to produce a "stationary" beam for integration time purposes.

Figures 2A, 2B:
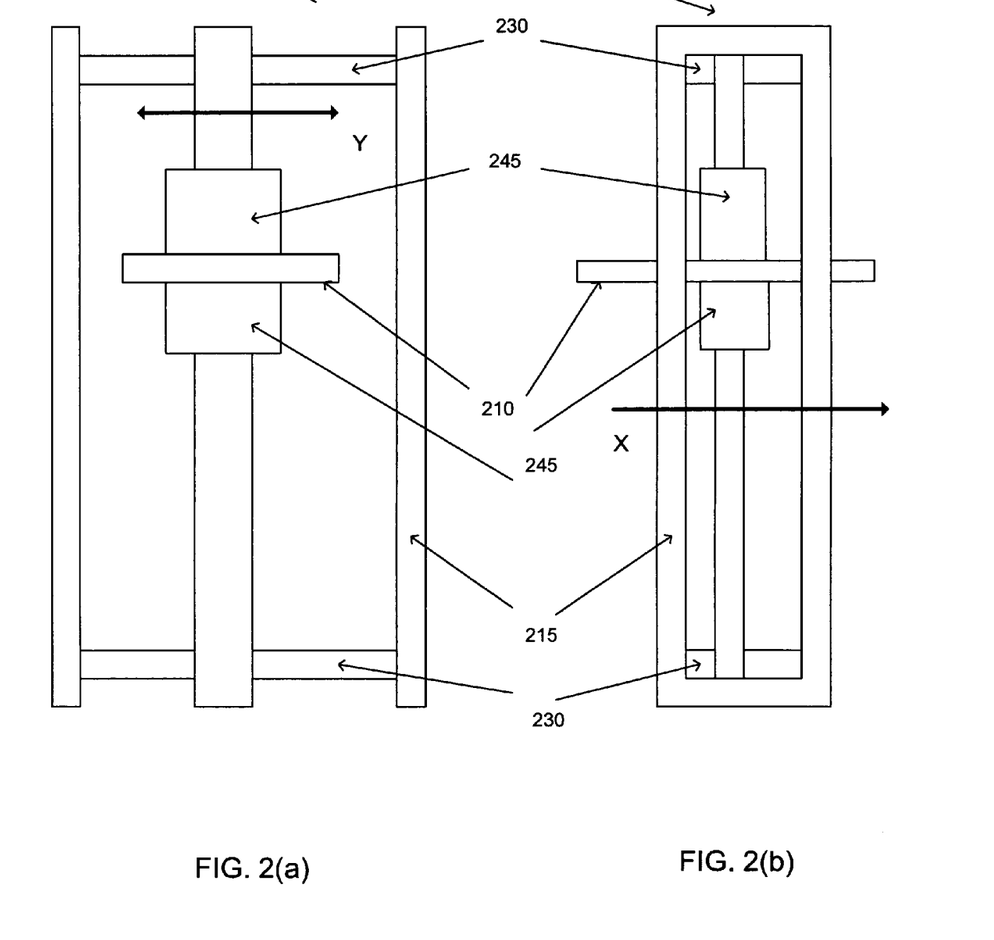
FIGS. 2(a) and 2(b) are schematic front and profile views respectively of a sheet making machine commonly used in the paper and plastics industries.

Referring to FIGS. 2(a) and 2(b) there is generally shown a schematic diagram of a sheet making machine 200. FIG. 2(a) is a front view of the sheet-making machine while FIG. 2(b) shows a profile view. A stationary frame 215 supports parallel guide members 230. Carriages 245 are mounted on the guide members 230 and contain spectrometer and other scanning components. The carriages 245 are configured to travel along a direction indicated by arrow Y back and forth across the sheet 210. The carriages 245 are connected to a drive system (not shown) which drives the carriage back and forth across the sheet 210 at a steady rate. Referring now to the profile view, FIG. 2(b), the sheet 210 is guided along a direction indicated by arrow X. The sheet may be driven by a drive system (not shown) at a steady rate.

Figure 3:
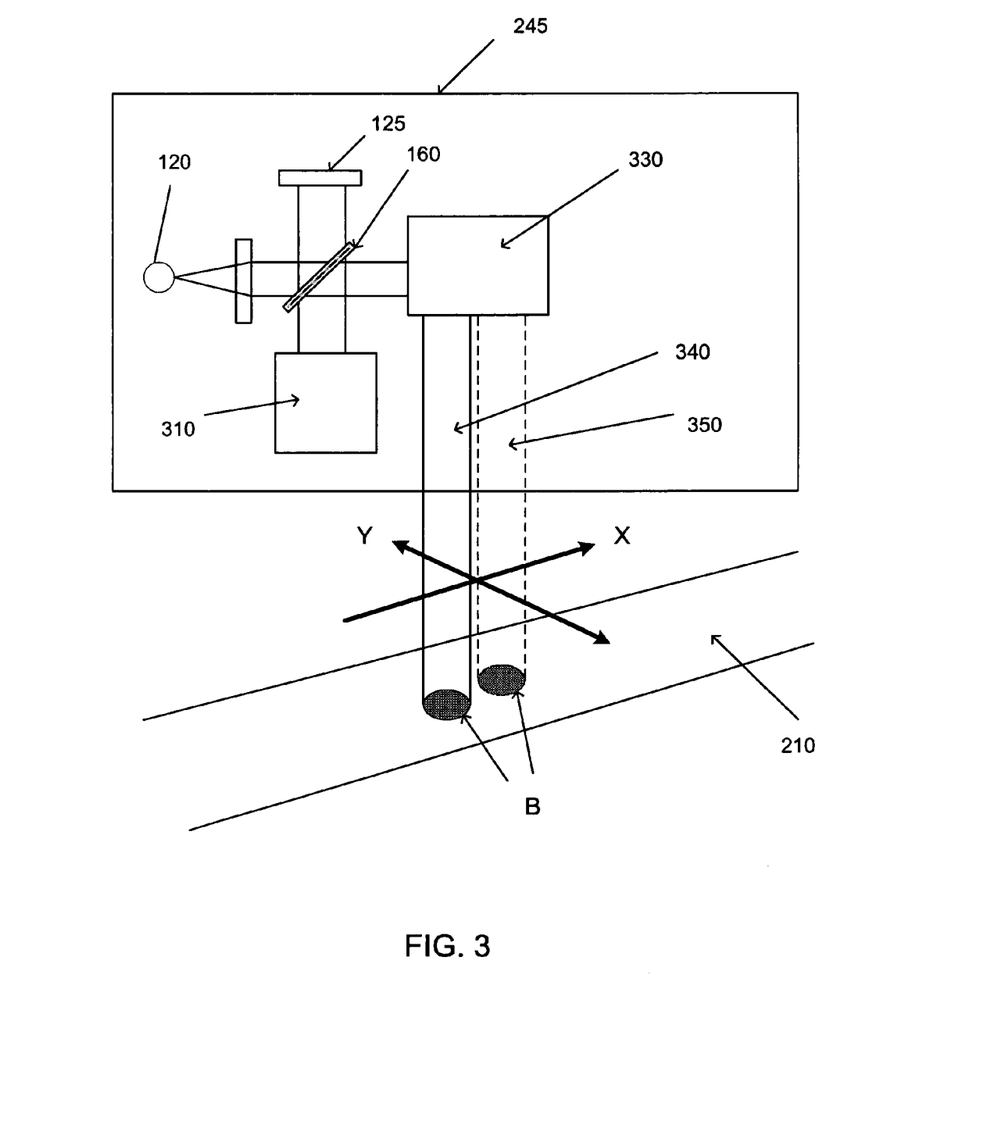
FIG. 3 is a schematic diagram of an optical scanner in accordance with an embodiment of the invention.

Referring now to FIG. 3, there is shown a schematic diagram of carriage 245 in accordance with an embodiment of the invention. In this particular case, the carriage 245 includes a FT-IR spectrometer configured to operate in reflection mode. The spectrometer includes an infrared source 120. The infrared source may be an incandescent source or a laser. While the specification will discuss exemplary embodiments configured with an infrared source, it will be understood that radiation in other parts of the spectrum may be used for detection of various characteristic properties of a sample. For instance, visible, near-IR, and mid-IR sensors may be used to measure different characteristic properties of a sample. Obviously, each part of the spectrum necessitates a source producing radiation in that part of the spectrum. For example, LED's may produce radiation in the visible spectrum, or laser which produce laser generated super continuum may produce radiation in a broad spectrum. Radiation from source 120 is collimated by a lens 140. The resultant beam (shown in solid lines) passes to and is divided by a beam splitter 160. Part of the beam is passed to a fixed beam dump 325, and another part of the beam is directed to a scanner 330.

The beam splitter 160 is configured so that the spectrometer receives the proper intended wide spectrum of the radiation. In one embodiment, the beam splitter is a half silver mirror. This may be a place of glass with a thin coating of silver (usually deposited from silver vapor) with the thickness of the silver coating such that, of light incident at a 45 degree angle, one half is transmitted and one half is reflected. Instead of a silver coating, a dielectric optical coating may also be used. In another embodiment, the beam splitter is a dichroic beam splitter which can be configured for high transmissivity for certain parts of the radiation spectrum and/or highly reflective of certain other parts of the radiation spectrum. One such beam splitter is disclosed in U.S. Pat. No. 6,961,126, entitled "Optical Wavelength Splitter,"which is herein fully incorporated by reference.

Beam dump 325 provides a "black"background so that any incident radiation on the beam dump is absorbed and does not further interfere with the source radiation. Thus, any part of the source beam that is reflected by the beam splitter 160 towards beam dump 325 is absorbed, and the remainder of the source beam passes through beam splitter 160 and reaches an optical scanner 330. The optical scanner 330 directs the beam 340 at a spot on the traveling sheet material 210. The beam is directed to spot B as indicated in the drawings, and as the beam is directed to compensate for the movement of the traveling sheet in the X direction and the movement of the carriage in the Y direction, the beam may move to a spot indicated by 350. It will be understood that beams 340 and 350 are not distinct beams, but indicate generally the movement of the beam 340 in different instances of time. The movement of the beam counteracts the movement of the sheet 210 and carriage 245 so that the resultant beam 350 is, in effect, stationary on the same spot of the moving sheet 210.

The beam path 340 impinges on the traveling web 210 and the radiation is reflected off the traveling web 210 back through the optical scanner 330 and reflected off the beam splitter 160 to the spectrometer 310. Since the beam spot B on the traveling sheet 210 remains stationary with respect to the sheet, the spectrometer has ample integration time period for creating a proper interference pattern.

The optical scanner may be coupled to electronic signals (not shown) indicative of the speed of the moving sheet in the X direction, and with the carriage speed in the Y direction. In practice, the speed of the moving sheet 210 may be predetermined by the manufacturing process and the speed of the carriage 245 may also predetermined by the manufacturing process. It will also be noted that because the speed of the optical scanner 330 is effectively negligible to the speed of the optical beam, for practical purposes, the reflected radiation follows the same optical path back to the interferometer or detector configuration.

Although, a spectrometer in reflection mode has been shown, it will be appreciated that the spectrometer may be operated in a transmission mode. In that mode of operation, the detector (interferometer) will typically be placed in the carriage 245 under the traveling sheet of material. It will be appreciated that such an arrangement will require that driving electronic signals (indicating the speed of the moving sheet and the speed of the carriage) be coupled to both the top and bottom parts of the carriage so that the detector be in absolute synchronization with the transmitting optical scanner. Such an arrangement may be necessary for measuring properties of sheet material which is highly translucent or where reflection spectra are negligible. It should be noted that such an arrangement requires that the detector configuration moves in sync with the beam movement.

Figure 4:
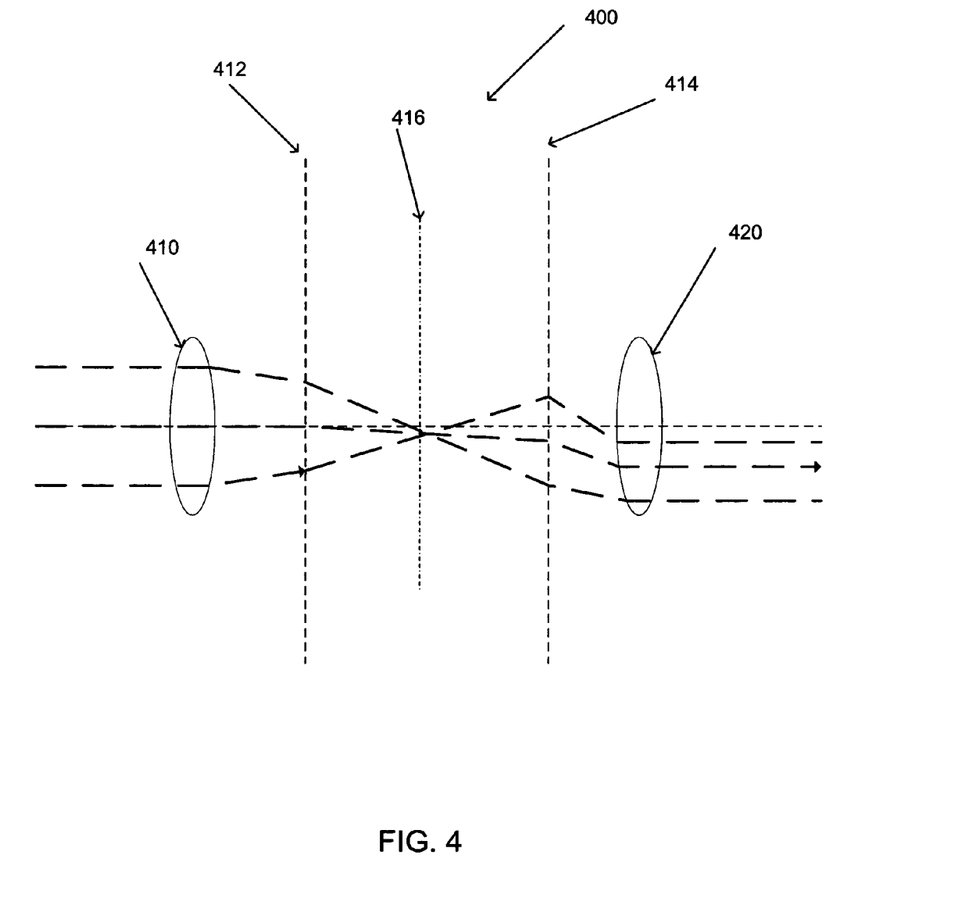
FIG. 4 is a schematic diagram of a galvanometer based optical scanner in accordance with an embodiment of the invention.

Details regarding the operation of the optical scanner 330 are discussed below. In one illustrative embodiment, the optical scanner is a galvanometer based optical scanner. In a galvanometer based optical scanner, the beam input into the optical scanner is moved across a directed plane by a beam-deflecting element such as a mirror which is angularly oscillated about an axis perpendicular to the optical beam axis. The oscillation is produced by a galvanometer type drive such as moving-coil, moving iron, or moving magnet drive. Such an arrangement is schematically illustrated in FIG. 4. Deflection axis 412 and 414 are formed by two beam deflecting elements such as mirrors. For illustrative purposes, the mirrors are placed close together to form a translation of the input optical beam in the same plane as the output optical beam. A focal axis 416 is the common focal point of the two lenses 410 and 420. The simple example shown in FIG. 4 illustrates that the beam (shown in dotted lines) entering lens 410 is translated along the same plane after departing lens 420.

Figure 5A:
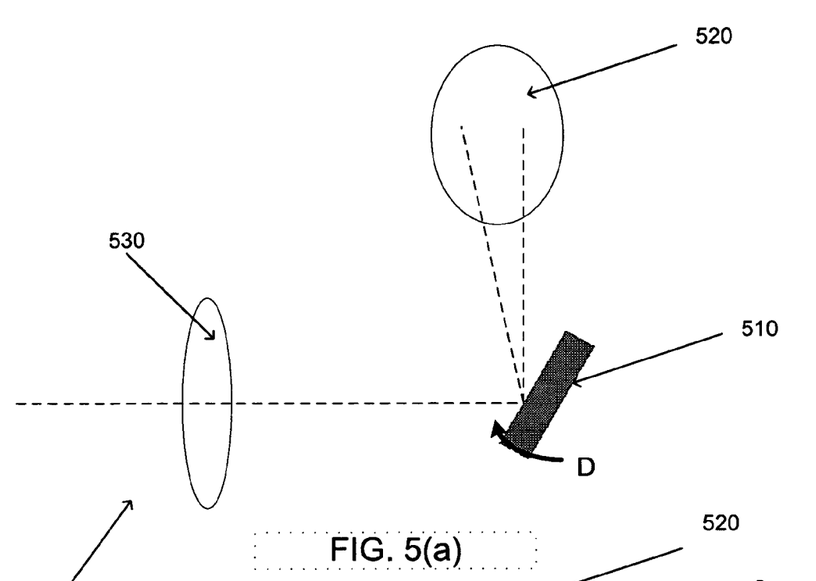
FIG. 5(a) and 5(b) are schematic front and profile views respectively of a galvanometer based optical scanner in accordance with an embodiment of the invention.
Figure 5B:
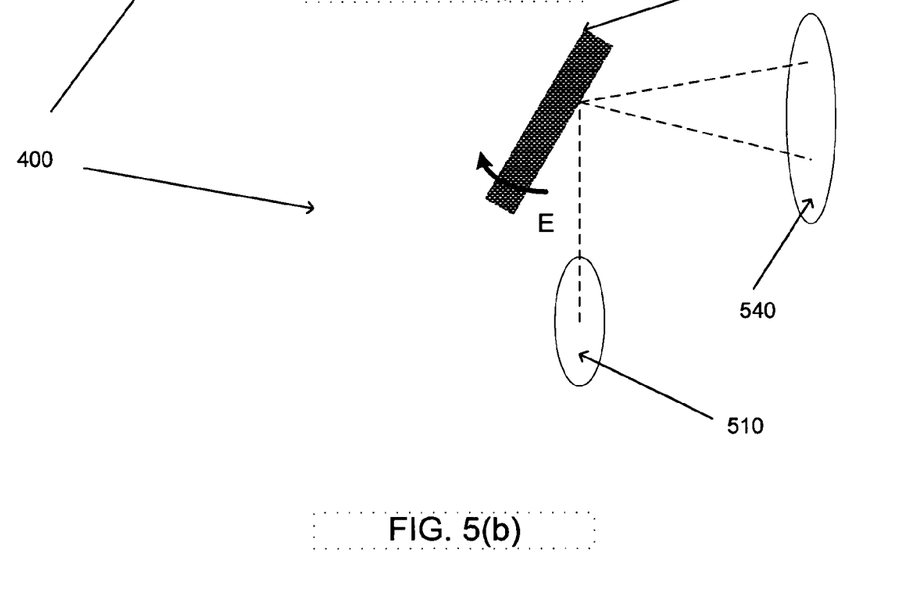

An implementation of the galvanometer based optical scanner 400 for scanning the optical beam in two dimensions is shown through profile views shown in FIGS. 5(a) and 5(b). A lens 530 directs a beam of radiation to a first mirror 510. The mirror 510 is oscillated based on a galvanometer about an axis indicated by D and serves to direct the beam (shown in dotted lines) to another mirror 520. The mirror 520 is oscillated about an axis indicated by E and serves to direct the beam to a lens 540. The disclosed galvanometer based arrangement translates the beam movement in two dimensions X and Y through two galvanometer based beam-deflecting elements.

The galvanometer driving the oscillation of mirror 510 is based on an electrical signal indicative of the speed of the traveling sheet 210. The galvanometer driving the oscillation of mirror 520 is based on an electrical signal indicative of the speed of the carriage as it traverses the traveling sheet 210. The embodiment disclosed is meant to be illustrative only, as other galvo-based scanning arrangements may be suitable for the desired purpose.

Figure 6:
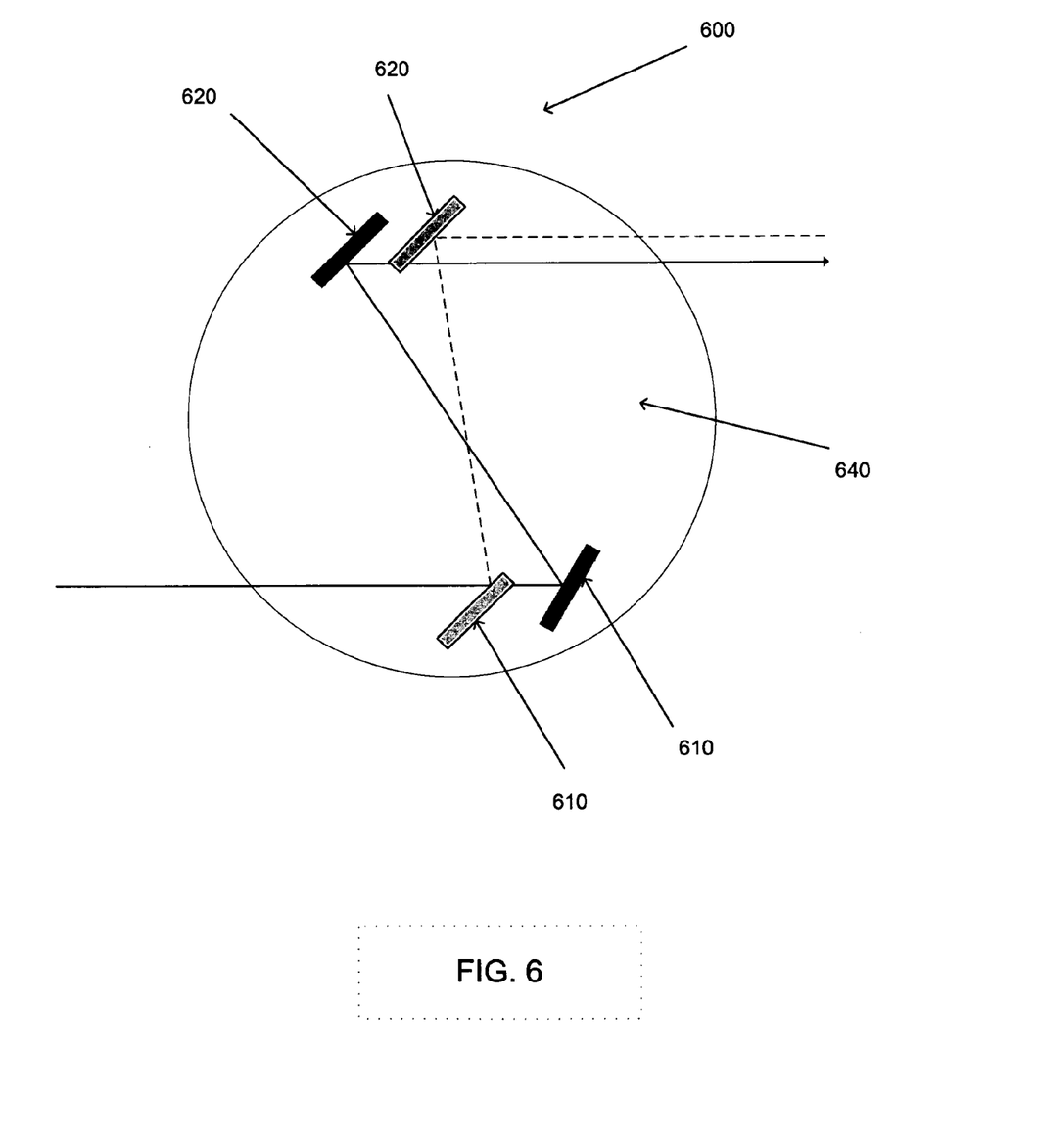
FIG. 6 is a schematic diagram of a spinning mirror based optical scanner in accordance with an embodiment of the invention.

Referring to FIG. 6, there is shown an alternative embodiment of the optical scanner in accordance with the invention. Two beam deflecting elements 610 and 620 are disposed in parallel on a spinning disc 640. An input beam (indicated in solid lines) impinges upon a mirror 610 in a first position (indicated by solid color) and the beam is deflected to the parallel mirror 620 in a first position (indicated by solid color). The beam is then deflected by mirror 620 to produce an output beam (indicated in solid lines).

As the disc 640 spins, the mirrors 610 and 620 are disposed at new positions (indicated by white boxes). The input beam impinges the mirror 610 at the new position and is deflected to the parallel mirror 620. The beam is then deflected by mirror 620 to produce an output beam (indicated by dotted lines). The spinning disc 640 is driven by an electrical signal indicative of the speed of the traveling sheet 210.

The disclosed embodiment shows a spinning mirror arrangement for translating an input beam in one dimension. Cascading the disclosed embodiment with another spinning mirror arrangement driven by an electrical signal indicative of the speed of the carriage will produce an optical beam translated in two dimensions. current signifying the speed of the traveling sheet of material.

The disclosed optical scanner arrangement has been illustrated with respect to a Fourier Transform Infrared Spectrometer. However, it will be understood that the optical scanner in one embodiment of the invention may be used, for instance, to measure the thickness of thin film products. A stationary spot is required for measuring the thickness in thin film products. Therefore, the technique involves keeping a stationary spot on one spot on the thin film and measuring the thickness by fitting a mathematical curve to the measurements taken by the spectrometer.

Additionally, although the optical scanner has been described with reference to a Fourier Transform Infrared Spectrometer, it will be understood that a conventional grating-based spectrometer coupled with a detector array may also be used.

The preferred embodiment of the present invention, an optical scanner for use in a spectrometer for measuring the properties of a traveling sheet of materials, is thus described. While the present invention has been described in particular embodiments, it should be appreciated that the present invention should not be construed as limited by such embodiments, but rather construed according to the below claims.

What is claimed is:

1. A spectrometer for measuring properties of traveling sheet material, said spectrometer comprising:
   a source for emitting optical radiation towards the traveling sheet material;
   a beam splitter for splitting the emitted optical radiation and the radiation after interaction with the traveling sheet material;
   a beam dump for absorbing any incident radiation that may interfere with the emitted optical radiation;
   an optical scanner for directing the emitted optical radiation towards the traveling sheet material; and
   a detector for measuring a resultant optical radiation after interaction with the traveling sheet material;

wherein the spectrometer generates, from said resultant optical radiation, an interferogram unique to the traveling sheet material, without the use of an ultrasonic signal directed to the traveling sheet material; and wherein said optical scanner is configured for scanning the radiation to counteract the movement of the traveling sheet material.

2. The spectrometer of claim 1, wherein said emitted optical radiation is infrared.

3. The spectrometer of claim 1, wherein said optical scanner is a galvanometer based optical scanner.

4. The spectrometer of claim 1, wherein said optical scanner is a spinning mirror.

5. The spectrometer of claim 1, wherein said optical scanner is configured for scanning the resultant optical radiation to counteract the movement of a carriage housing the spectrometer.

6. The spectrometer of claim 1, wherein said beam splitter is a half-silver mirror.

7. The spectrometer of claim 1, wherein said beam splitter is a dichroic beam splitter.

8. The spectrometer of claim 1, wherein said optical scanner scans the radiation to the same spot on the traveling sheet material.

9. The spectrometer of claim 3, said galvanometer based optical scanner further comprising:
a first oscillating mirror for translating the radiation in a first dimension; and
a second oscillating mirror for translating the radiation in another dimension orthogonal to the first dimension.

10. The spectrometer of claim 9, wherein said first oscillating mirror is driven by a galvanometer responsive to a signal representative of the speed of the traveling sheet material.

11. The spectrometer of claim 10, wherein said second oscillating mirror is driven by a galvanometer responsive to a signal representative of the speed of a carriage housing the spectrometer.

12. The spectrometer of claim 4, said optical scanner further comprising:
a plurality of mirrors disposed in parallel to each other, said plurality of mirrors disposed on a spinning disc.

13. The spectrometer of claim 12, wherein said spinning disc is driven by a signal representative of the speed of the traveling sheet material.

14. The spectrometer of claim 12, wherein said spinning disc is driven by a signal representative of the speed of a carriage housing the spectrometer.

15. An optical scanner for use in conjunction with a spectrometer, said spectrometer configured for measuring properties of traveling sheet material, said spectrometer comprising a radiation source for emitting optical radiation, a beam splitter for splitting the emitted optical radiation, and a detector for measuring a resultant optical radiation after interaction with the traveling sheet material, said spectrometer generating from the resultant optical radiation an interferogram unique to the traveling sheet material without the use of an ultrasonic signal directed to the traveling sheet material; said optical scanner comprising:
oscillating beam deflecting means for keeping a beam of the radiation stationary with respect to the traveling sheet material; and
driving means for driving said oscillating beam deflecting means.

16. The optical scanner of claim 15, wherein said driving means is responsive to an electrical signal indicative of the speed of the traveling sheet material.

17. The optical scanner of claim 15, wherein said driving means is responsive to an electrical signal indicative of the speed of a carriage housing said spectrometer.

18. The optical scanner of claim 15, wherein said oscillating beam deflection means translates the beam of radiation in two dimensions.

19. The optical scanner of claim 15, wherein said oscillating beam deflection means deflects the beam in a direction parallel to the beam of radiation.

20. The optical scanner of claim 15, wherein said oscillating beam deflection means keeps the beam stationary with respect to a carriage housing said spectrometer.

21. The optical scanner of claim 15, wherein said oscillating beam deflection means is a minor.

22. The optical scanner of claim 15, wherein said driving means is a galvanometer.

* * * * *